US00PP16410P2

(12) United States Plant Patent
Hooijman

(10) Patent No.: US PP16,410 P2
(45) Date of Patent: Apr. 4, 2006

(54) ***ASTER* PLANT NAMED 'ESMALL'**

(50) Latin Name: *Aster hybrida*
Varietal Denomination: Esmall

(75) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 134 days.

(21) Appl. No.: 10/783,492

(22) Filed: Feb. 21, 2004

(51) Int. Cl.
*A01H 5/00* (2006.01)

(52) U.S. Cl. ..... Plt./355
(58) Field of Classification Search ..... Plt./355
See application file for complete search history.

(56) References Cited

PUBLICATIONS

UPOV–ROM GTTM 2005 Jouve retrieval; cultivar Esmall.*

* cited by examiner

*Primary Examiner*—Bruce R. Campell
*Assistant Examiner*—S B McCormick-Ewoldt
(74) *Attorney, Agent, or Firm*—C. A. Whealy

(57) ABSTRACT

A new and distinct cultivar of cut flower *Aster* plant named 'Esmall', characterized by its strong erect flowering stems; symmetrical branching habit; small dark green-colored foliage; uniform and freely flowering habit; decorative-type inflorescences with purple-colored ray florets; and good postproduction longevity.

1 Drawing Sheet

Botanical classification/cultivar designation: *Aster hybrida* cultivar Esmall.

BACKGROUND OF THE INVENTION

The present Invention relates to a new and distinct cultivar of cut flower *Aster* plant, botanically known as *Aster hybrida* and hereinafter referred to by the name 'Esmall'.

The new *Aster* is a product of a planned breeding program conducted by the Inventor in El Quinche, Pichincha, Ecuador. The objective of the breeding program is to create new cut flower *Aster* cultivars with durable leaves, strong stems, desirable floret colors, and good postproduction longevity.

The new *Aster* originated from a cross-pollination made by the Inventor in El Quinche, Pichincha, Ecuador in August, 1999, of a proprietary *Aster* selection identified as Code 70, not patented, as the female, or seed, parent with an unknown *Aster* selection, not patented, as the male, or pollen, parent. The new *Aster* was discovered and selected by the Inventor as a single flowering plant within the progeny of the stated cross-pollination grown in a controlled environment in El Quinche, Pichincha, Ecuador. The selection of this plant was based on its durable foliage, strong stems and desirable inflorescence form and ray floret color.

Asexual reproduction of the new *Aster* by vegetative tip cuttings was first conducted in El Quinche, Pichincha, Ecuador in August, 2000. Asexual reproduction by cuttings has shown that the unique features of this new *Aster* are stable and reproduced true to type in successive generations.

SUMMARY OF THE INVENTION

The cultivar Esmall has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Esmall'. These characteristics in combination distinguish 'Esmall' as a new and distinct cut flower *Aster:*

1. Strong erect flowering stems.
2. Symmetrical branching habit.
3. Small dark green-colored leaves.
4. Uniform and freely flowering habit.
5. Decorative-type inflorescences with purple-colored ray florets.
6. Good postproduction longevity.

Plants of the new *Aster* are most similar to plants of the female parent selection. Plants of the new *Aster* differ from plants of the female parent selection primarily in plant height as plants of the new *Aster* are taller than plants of the female parent selections.

Plants of the new *Aster* can be compared to plants of the cultivar Cirina, not patented. In side-by-side comparisons conducted in El Quinche, Pichincha, Ecuador plants of the new *Aster* differed from plants of the cultivar Cirina in the following characteristics:

1. Plants of the new *Aster* were not as broad as plants of the cultivar Cirina.
2. Plants of the new *Aster* flowered about one week earlier than plants of the cultivar Cirina.
3. Plants of the new *Aster* were more freely flowering than plants of the cultivar Cirina.
4. Plants of the new *Aster* had longer inflorescences than plants of the cultivar Cirina.
5. Plants of the new *Aster* and the cultivar Cirina differed in ray floret coloration as plants of the cultivar Cirina had purple violet-colored ray florets.

BRIEF DESCRIPTION OF THE PHOTOGRAPHS

The accompanying colored photographs illustrate the overall appearance of the new *Aster* showing the colors as true as it is reasonably possible to obtain in colored reproductions of this type. Colors in the photographs may differ from the color values cited in the detailed botanical description which accurately describe the colors of the new *Aster*.

The photograph at the top of the sheet comprises a side perspective view of a typical flowering plant of 'Esmall'.

The photograph at the bottom of the sheet comprises a close-up view of typical inflorescences of 'Esmall'.

DETAILED BOTANICAL DESCRIPTION

In the following description, color references are made to The Royal Horticultural Society Colour Chart, 2001 Edition, except where general terms of ordinary dictionary significance are used. The aforementioned photographs, following observations and measurements describe plants grown and flowered during the fall in El Quinche, Pichincha, Ecuador, in an outdoor nursery and under conditions which approximate those generally used in commercial cut flower *Aster* production. During the production of these plants, day temperatures ranged from 11 to 30° C. and night temperatures ranged from 5 to 12° C. Plants were about four to six months from planting rooted young plants when the photographs and the botanical description were taken.

Botanical classification: *Aster hybrida* cultivar Esmall.

Parentage:

*Female, or seed, parent.*—Proprietary *Aster hybrida* selection identified as Code 70, not patented.

*Male, or pollen, parent.*—Unknown *Aster hybrida* selection, not patented.

Propagation:

*Type.*—Terminal vegetative cuttings.

*Time to initiate roots.*—About 12 to 16 days at 17 to 25° C.

*Time to produce a rooted young plant.*—About 21 to 25days at 17 to 25° C.

*Root description.*—Fine, fibrous; 161D in color.

*Rooting habit.*—Freely branching.

Plant description:

*Appearance.*—Herbaceous decorative-type cut flower *Aster*. Flowering stems upright and strong. Vigorous. Symmetrical branching habit.

*Plant height.*—About 118 cm.

*Plant width.*—About 17 cm.

*Lateral branches.*—Quantity per plant: About 31. Length: About 116 cm. Diameter: About 6.9 mm. Internode length: About 2.1 cm. Strength: Strong. Texture: Glabrescent; waxy. Color: 144B.

*Foliage description.*—Arrangement: Alternate, simple; sessile. Quantity per lateral branch: About 293. Length: About 13.6 cm. Width: About 1.2 cm. Shape: Lanceolate. Apex: Acute. Base: Cordate. Margin: Minutely dentate. Texture, upper and lower surfaces: Glabrous, smooth; waxy. Color: Developing foliage, upper surface: 137A. Developing foliage, lower surface: 137B. Fully expanded foliage, upper surface: 137B; venation, 147B. Fully expanded foliage, lower surface: 137C; venation, 147B.

Inflorescence description:

*Appearance.*—Decorative-type inflorescence form with narrowly elliptic-shaped ray florets. Inflorescences terminal or axillary. Disk and ray florets develop acropetally on a capitulum. Inflorescences not fragrant. Inflorescences persistent. Inflorescences face mostly upright. Uniform and freely flowering habit.

*Flowering response.*—Plants flower year-round in Ecuador.

*Postproduction longevity.*—Inflorescences maintain good color and substance for about two weeks as a cut flower and about 25 days on the plant.

*Quantity of inflorescences.*—About 26 inflorescences develop per lateral branch.

*Inflorescence bud.*—Height: About 6 mm. Diameter: About 5.3 mm. Shape: Nearly globose. Color: 132A to 132B.

*Inflorescence size.*—Diameter: About 3 cm. Depth (height): About 1.2 cm. Diameter of disc: About 1 cm. Receptacle height: About 5 mm. Receptacle diameter: About 8 mm.

*Ray florets.*—Number of ray florets per inflorescence/arrangement: About 37 in arranged in two whorls. Length: About 1.3 cm. Width: About 2 mm. Shape: Narrowly elliptic. Apex: Obtuse with emarginations. Base: Attenuate. Margin: Entire. Texture, upper and lower surfaces: Smooth, glabrous; papery. Orientation: Initially upright, then mostly horizontal. Aspect: Mostly straight. Color: When opening, upper surface: N78A to N80A. When opening, lower surface: 77A to N80A. Fully opened, upper surface: Closest to N78A. Fully opened, lower surface: 77A to N80A.

*Disc florets.*—Arrangement: Massed at center of receptacle. Number of disc florets per inflorescence: About 43. Length: About 8.5 mm. Diameter, apex: About 1.8 mm. Diameter, base: About 1.6 mm. Shape: Tubular, salverform, elongated. Apex: Acute. Color, immature: 178A. Color, mature: 145C.

*Phyllaries.*—Quantity per inflorescence: About 34. Length: About 7 mm. Width: About 1.2 mm. Shape: Narrowly deltoid. Apex: Acute. Base: Truncate. Texture, upper and lower surfaces: Smooth, glabrous. Color, upper surface: 137B. Color, lower surface: 137C.

*Peduncles.*—Length, terminal peduncle: About 1.9 cm. Length, fourth peduncle: About 2.6 cm. Length, seventh peduncle: About 4.4 cm. Diameter: About 1.2 mm. Aspect: Erect to about 31° from vertical. Strength: Strong. Texture: Pubescent. Color: 137D.

*Reproductive organs.*—Androecium: Present on disc florets only. Quantity per disc floret: One. Anther shape: Linear. Anther length: About 1 mm. Anther color: Bicolored, 7B and 59B. Pollen amount: Scarce. Pollen color: 7B. Gynoecium: Present on both ray and disc florets. Quantity per floret: One. Pistil length: About 5.6 mm. Stigma shape: Bilobed. Stigma color: 59A. Style length: About 4.4 mm. Style color: 145C. Ovary color: Bicolored, 192D and 145D.

*Seed.*—Length: With pappus, about 5 mm; without pappus, about 3 mm. Diameter: About 1 mm. Color: 145D; dried, 199A.

Disease/pest resistance: Resistance to pathogens and pests common to *Asters* has not been observed on plants grown under commercial greenhouse conditions.

Temperature tolerance: Plants of the new *Aster* have been observed to tolerate temperatures from 7 to over 30° C.

It is claimed:

1. A new and distinct cultivar of cut flower *Aster* plant named 'Esmall', as illustrated and described.

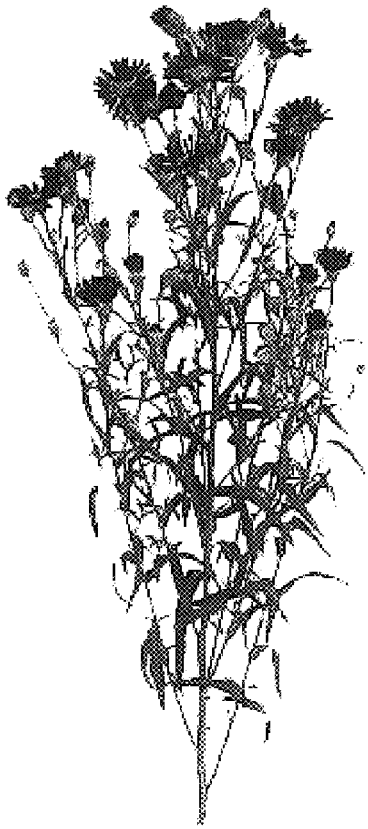
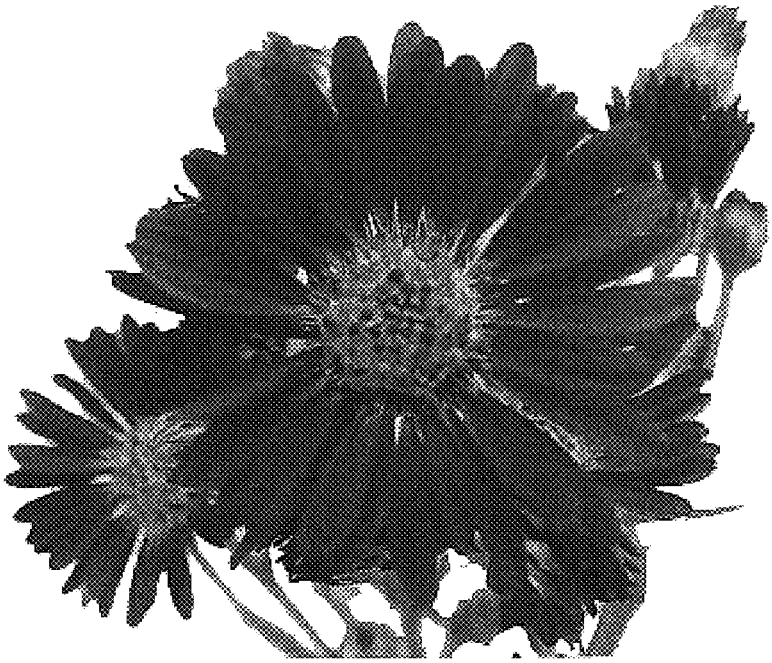

* * * * *